United States Patent [19]

Bews et al.

[11] Patent Number: 4,659,560

[45] Date of Patent: Apr. 21, 1987

[54] DEODORANT COMPOSITIONS

[75] Inventors: Brian Bews, Isleworth; Peter Critchley, Camberley; James A. Durrant, Bedfont; Malcolm R. D. Stebles, Maidenhead; Leigh R. H. Tipping, Twickenham, all of England

[73] Assignee: Lever Brothers Company, New York, N.Y.

[21] Appl. No.: 710,954

[22] Filed: Mar. 14, 1985

Related U.S. Application Data

[63] Continuation of Ser. No. 287,006, Jul. 27, 1981, abandoned, which is a continuation of Ser. No. 175,229, Aug. 5, 1980, abandoned.

[30] Foreign Application Priority Data

Aug. 10, 1979 [GB] United Kingdom ................. 7927924
Aug. 10, 1979 [GB] United Kingdom ................. 7927922
Aug. 10, 1979 [GB] United Kingdom ................. 7927920

[51] Int. Cl.$^4$ ............................ A61K 7/32; A61K 9/12
[52] U.S. Cl. ................................ 424/47; 424/DIG. 5; 424/65; 424/78
[58] Field of Search ............................ 424/65, 68, 47

[56] References Cited

U.S. PATENT DOCUMENTS

| | | | |
|---|---|---|---|
| 1,907,424 | 5/1933 | Manning | 424/68 |
| 2,350,047 | 5/1944 | Klarmann et al. | 424/68 |
| 2,373,198 | 4/1945 | Roehrich | 424/68 |
| 2,571,030 | 10/1951 | Govett et al. | 424/68 |
| 2,653,902 | 9/1953 | Thurmon | 424/68 |
| 2,664,581 | 1/1954 | Miller et al. | 424/65 |
| 3,317,372 | 5/1967 | Hart | 424/65 |
| 4,090,013 | 5/1978 | Ganslaw | 526/15 |

FOREIGN PATENT DOCUMENTS

| | | | |
|---|---|---|---|
| 763973 | 2/1934 | France | 424/65 |
| 2250516 | 6/1975 | France | 424/69 |
| 2269924 | 12/1975 | France | 424/67 |
| 427597 | 4/1935 | United Kingdom | 424/65 |
| 437865 | 11/1935 | United Kingdom | 424/65 |
| 820315 | 9/1959 | United Kingdom | 424/69 |
| 966560 | 6/1965 | United Kingdom | 424/65 |
| 1456200 | 11/1976 | United Kingdom | 424/65 |

OTHER PUBLICATIONS

J. S. Jellinek's "Kosmetologie", 2nd Edition, 1967, pp. 211-213, chapter 4.
"Harry's Cosmeticology", 6th Edition, Leonard Hill Books, 1973, pp. 270-274.
Ikai, Journ. of Investigative Dermatology, 1954, vol. 23, pp. 411 to 422.
Derwent Abstract No. 26870B/14, Abstract of Japanese Pat. No. 091219, 7/28/77.
Derwent Abstract No. 22620W/14, Abstract of German Pat. No. 2341938, 8/20/73.
Derwent Abstract of Japanese Pat. No. 134889, 10/31/78.
Derwent Abstract of Japanese Pat. No. 137164, 11/06/78, Abstract No. 44402C/25.

*Primary Examiner*—Dale R. Ore
*Attorney, Agent, or Firm*—Milton L. Honig; James J. Farrell

[57] ABSTRACT

The invention provides a deodorant composition for reducing axillary body odor without suppressing the secretion of perspiration, comprising a suspension of a particulate deodorant active material in a carrier liquid or gel medium containing less than 80% water by weight of the carrier medium, particularly an aerosol or roll-on composition, in which the deodorant active ingredient is an oxide, hydroxide or carbonate of magnesium or lanthanum or a mixture thereof.

14 Claims, No Drawings

DEODORANT COMPOSITIONS

This is a continuation application of Ser. No. 287,006, filed July 27, 1981 which is a continuation of Ser. No. 175,229, filed Aug. 5, 1980, both abandoned.

This invention relates to deodorant compositions and more particularly to compositions for reducing axillary odour.

It is well known that the unpleasant odour that develops in the axillae is due to the bacterial decomposition of apocrine sweat. There are a large number of products on the market for treating the problem of malodorous perspiration and the most popular product forms are lotions, usually applied from a roll-on applicator, and aerosols. Many such products contain ingredients which reduce the amount of perspiration secreted, ie they are antiperspirants. Most antiperspirant agents employed are astringent aluminium compounds, the use of an aluminium hydroxychloride being very common. Astringent aluminium compounds also have a deodorant effect on the perspiration that is secreted.

The present invention is concerned with compositions that have only a deodorant effect, that is they do not check the flow of perspiration to any appreciable extent. The composition and mode of action of deodorants has been discussed in the article "Deodorants and Antiperspirants" by Joseph R. Robinson in the "Handbook of Non-Prescription Drugs", 1973 Edition, Page 209 edited by G. B. Griffenhagen and L L Hawkins, Washington, DC, American Pharmaceutical Association. This article gives the active ingredients used in many brands of deodorant products.

Many accounts of the origin of unpleasant body odours state that they are caused by the bacterial decomposition of apocrine sweat (e.g. "Cosmetics and the Skin" by Wells and Lubowe, Page 290, (1964)) and it has been stated that a satisfactory deodorant product must contain an effective antibacterial agent ("Cosmetics Science and Technology", Second Edition, Volume 2 (1972) p 400). Many actual products have been based on the use of germicides such as hexachlorophene and various quaternary ammonium compounds.

However, in the past other methods of combatting body odour have been proposed. For example, the use of ion-exchange resins for adsorbing odorous substances found in axillary sweat has been suggested (U.S. Pat. No. 2,653,902 (1955); J.invest. Derm. 23,411 (1954) and J.Soc. Cosmet. Chemists 7, 256 (1956)), but no product using ion-exchange resins as deodorants has been marketed ("Cosmetics Science and Technology, Second Edition, Volume 2 (1972), page 403). A further method consists in masking unpleasant body odours with pleasant ones ("Formulation and Function of Cosmetics" by Dr J. Stephen Jellinek (1970), page 291). The use of antibiotics has also been suggested ("Cosmetics Science and Technology" Second Edition, Volume 2 (1972), page 402).

Recently other deodorising compounds that have been suggested are: calcium, aluminium, magnesium or zinc salts of unsaturated aliphatic hydroxycarboxylic acids having at least 17 carbon atoms, such as zinc ricinoleate (British specification No. 1 282 889); esters of a mono or dibasic aliphatic acid and having 2 to 4 carbon atoms with an aliphatic or alicyclic alcohol having from 1 to 6 carbon atoms (British specification No. 1 487 293); $C_1$–$C_6$ alkyl esters of certain alkanediphosphonic acid esters (British specification No. 1 524 167); and zinc and magnesium salts of certain polycarboxylic acids such as the dimers and trimers of linoleic and linolenic acid (British specification No. 2 014 453).

Although so far as actual commercially marketed personal deodorants are concerned, these have mainly been based on the use of bactericides, it has been felt that the continuous use of such agents is not without some risk of damage to the natural skin functions (see British specification Nos. 1 282 889, 1 487 293, 1 524 167 and 2 014 453).

It is an object of the present invention to provide a new deodorant composition for reducing axillary odour in the form of a lotion, gel or aerosol which composition comprises an active ingredient which is neither an astringent nor bactericidal. It is also an object to provide a composition having an active ingredient capable of giving a deodorant effect over a substantial period of about 24 hours or more, and which has the further advantages of being colourless, odourless and free of undesirable side effects.

According to the invention there is provided a deodorant lotion, stick or aerosol composition for reducing axillary body odour without suppressing the secretion of perspiration, comprising a suspension of a particulate deodorant active material in a carrier liquid or gel medium containing less than 80% water by weight of the carrier medium, characterised in that the deodorant active ingredient is an oxide, hydroxide or carbonate of magnesium or lanthanum or a mixture thereof.

It will be understood from the above that the deodorant composition of this invention is to be distinguished from an antiperspirant composition also having a deodorant effect. The active ingredient of the composition of the present invention has only a deodorant effect. Thus the deodorant compositions of this invention are distinguished from the aqueous antiperspirant compositions described in U.S. Pat. No. 2,350,047 which also contain in order to retard the deteriorating corrosive effect on fabric of the antiperspirant aluminium compound, an oxide, hydroxide or carbonate of zinc, magnesium or aluminium.

It is also to be noted that the compositions of the present invention are also distinguished from the body or dusting powders formulations which usually consist of a talc base and which may also contain other powdered ingredients such as magnesium carbonate ("Harry's Cosmeticology" revised by J. B. Wilkinson (1973), p 249). Magnesium carbonate has been included in such preparations as a carrier for perfume ("The Principles and Practice of Modern Cosmetics "by R. G. Harry, First Edition (1948) Volume 2, p. 183, and "Perfumes Cosmetics and Soaps" by W. A. Poucher, 2nd Edition (1925) Volume 1, p. 179).

Although a deodorant effect by a talc powder containing magnesium carbonate or oxide of high surface area as well as by other powders having a large surface area has been predicted in "Der Schweiss" by H. P. Fiedler (1968) page 416, simply on the basis of the adsorbent properties of large surface area powders, no deodorant effect by such a powder has been found. An ability to absorb and bind specific odorous materials is required and butylamine and ethyl mercaptan have been suggested as model compounds with which to assess the potential absorptivity of body deodorant active material (British specification No. 2 014 453). Indeed, the addition of deodorants effective against body odours to powders containing a proportion of magnesium carbonate has been suggested (British specifications Nos. 1 282 889 and 1 524 167).

The deodorant composition of the invention may be in the form of a lotion, the carrier liquid for such type of product usually being a volatile alcohol preferably ethanol or a mixture thereof with water, the amount of water preferably being less than 60% by weight of the carrier medium. Other suitable carrier liquids are well known to those in the art. Deodorant lotions are commonly applied to the skin from a roll-on applicator although they may be applied from other applications. The liquid phase also usually comprises an emollient material to provide desirable skin-feel qualities and help to retain the deodorant active material on the skin. Especially suitable is isopropyl myristate or other fatty acid esters, such as di-butyl phthalate and di-isopropyl adipate, but other materials well-known to those skilled in the art can also be used, for example cetyl alcohol.

To assist in maintaining the deodorant powder in suspension in the lotion a thickening agent is desirably included. Preferably, a hydrophobic clay or colloidal silica is used for this purpose. Hydrophobic clays are available under the trade name Bentone, e.g. Bentone-34 or Bentone-38. Suitable colloidal silicas include Aerosil 200 and Cab-O-Sil M-5 as well as other grades. Cellulose derivatives, e.g. hydroxypropyl celluloses (such as Klucel M), can also be used.

Roll-on compositions in accordance with the invention will usually comprise 10–30% deodorant active powder, 1–30% emollient, 0.5 to 5% suspending agent, with the balance consisting essentially of alcohol or aqueous alcohol.

Deodorant products of the invention in gel form will comprise the usual ingredients to provide a stick base within which the particulate deodorant active ingredient is dispersed. Such bases usually comprise alcohol or aqueous alcohol thickened to form a gel with sodium stearate or other hard soaps. The gel preferably also includes materials to improve the skin-feel, such as glycerol. These compositions will usually contain about 10 to 30% by weight of the powdered deodorant active ingredient.

The deodorant composition may also be in the form of an aerosol, the composition being packaged in an aerosol container together with a gaseous propellant. The aerosol composition may be of the type which a powder is suspended in a liquid vehicle comprising a mixture of a carrier liquid and a liquefied gaseous propellant.

Aerosol compositions of the powder suspension type are well known to those skilled in the art. Conventional carrier liquids and liquefied propellants can be used in aerosol compositions of this invention along with a conventional suspending agent which is frequently included in such products to assist in the suspending of the active powdered ingredient. In particular, the formulation of antiperspirant powder suspension aerosol compositions is well known, and the formulation of the deodorant products of this invention can be effected by replacing the powdered antiperspirant active ingredient of such products by a powder of one or more of the above deodorant active compounds. An aerosol powder suspension product in which the active powder ingredient is a deodorant is described in British patent specification No. 1 476 117. In the product described in this prior specification the deodorant active material is an alkali metal bicarbonate. Deodorant products in accordance with the present invention may be made by replacing the sodium bicarbonate in the examples in specification No. 1 476 117 by a powder of an oxide, hydroxide or carbonate of magnesium or lanthanum or mixture thereof.

The amount of powdered deodorant active material present in an aerosol composition of the invention may vary over a wide range but will usually be in the range 0.5 to 15% by weight of the composition. Preferred amounts are from about 1% to about 10% by weight of the aerosol composition, particularly 1.5% to 5% by weight. The deodorant powder desirably comprises particles less than 100 microns in diameter and preferably is composed essentially of particles having a size of from 10 to 70 microns.

The carrier liquid may for example be a non-volatile non-hygroscopic liquid as suggested in U.S. Pat. No. 3,968,203. Especially useful are carrier liquids which have emollient properties and a number of these are referred to in British patent specification No. 1,393,860. Especially preferred are fatty acid esters such as isopropyl myristate and those esters referred to in U.S. Pat. No. 4,045,548 such as dibutyl phthalate and diisopropyl dipate.

Various other carrier liquids for powder suspension aerosols are suggested in U.S. Pat. Nos. 3,974,270, 3,949,066, 3,920,807, 3,833,721 and 3,833,720, and in British patent specification Nos. 1,411,547, 1,369,872, 1,341,746, 1,500,260 and 1,476,117. Volatile carrier liquids which may be used such as ethanol are also described in South African patent specification No. 75/3576, and the use of volatile silicones is described in British patent specification No. 1,467,676.

The ratio of the weight of the deodorant active powder to the carrier liquid may vary over a wide range, for example from 0.01 to 3 parts, preferably 0.04 to 1 part, of the powder per part by weight of the carrier liquid.

The liquefied propellant can be a hydrocarbon, a halogenated hydrocarbon or a mixture thereof. Examples of materials that are suitable for use as propellants are given in the above-mentioned patents and include trichlorofluoromethane, dichlorodifluoromethane, dichlorotetrafluoroethane, monochlorodifluoromethane, trichlorotrifluoroethane, propane, butane, 1,1-difluoroethane, 1,1-difluoro-1-chloroethane, dichloromonofluoromethane, methylene chloride, and isobutane, used singly or admixed. Trichlorofluoromethane, dichlorodifluoromethane, dichlorotetrafluoroethane, and isobutane, used singly or admixed, are preferred.

It is common practice to include in aerosol powder spray compositions a material to assist in the suspending of the powder in the liquid vehicle. The materials prevent compacting of the powder and they may also act as thickening or gelling agents for the liquid vehicle. Especially preferred are hydrophobic clays and colloidal silicas. Hydrophobic clays are available under the trade name Bentone, eg Bentone-34 or Bentone-38, and their use as suspending agents is described in a number of patent specifications including U.S. Pat. No. 3,773,683. Suitable colloidal silicas include Aerosil 200 and Cab-O-Sil M-5 as well as other grades. The use of hydrophobic clays and collidal silicas for suspending a powder in the production of an aerosol deodorant spray is also described in British specification No. 1 476 117.

Recently it has been disclosed in British patent specification Nos. 1 485 373, 1 501 862 and 2 003 730 that the manifestation of perspiration on the skin can be limited without the use of astringent perspiration depressants by application of a solid particulate moisture-absorbing polymer which has the capacity to absorb an amount of moisture at least equal to its own weight.

Such water-swellable absorbent polymers may be included in those deodorant compositions of the invention described above which utilise an anhydrous or substantially anhydrous carrier medium.

The anionic polyelectrolyte absorbent material may for example be a cross-linked etherified starch as described in German Application specification No. 2 702 781 or U.S. Pat. No. 4,117,222; a cross-linked sodium carboxymethyl cellulose as described in U.S. Pat. Nos. 3,589,364, 3,936,441 or 3,965,091; an internally esterified polyelectrolyte as described in U.S. Pat. No. 3,678,031; or a starch-acrylonitrile graft copolymer as described in U.S. Pat. Nos. 3,997,484 or 3,661,815; or a poly-acrylate cross-linked with a polyamide/epichlorhydrin material as described in German patent application No. 2 614 662; or a potassium salt of a polyacrylic acid cross-linked by aluminium ions as described in U.S. Pat. No. 4,090,013. They are insoluble in water to an extent of at least 40% by weight.

According to a further aspect of the invention therefore there is provided an aerosol product of the powder suspension type in which a powder is suspended in a liquid vehicle comprising a mixture of a liquid carrier and a liquid propellant, characterised in that the powder comprises a mixture of a water-absorbent anionic polyelectrolyte and an oxide, hydroxide or carbonate of magnesium or lanthanum or a mixture thereof. These aerosol compositions desirably contain from 0.5 to 15% by weight of the water-absorbent anionic polyelectrolyte and 0.5 to 15% by weight of the deodorant active powder.

The water-absorbent anionic polyelectrolyte may also be included in anhydrous or substantially anhydrous lotion or gel type deodorant products of the invention. In such products the polyelectrolyte is preferably present in an amount of 10 to 30%, preferably 15 to 25% by weight.

Deodorant compositions in accordance with the invention preferably also include a perfume but may also include other optional minor ingredients. Perfumes are generally included in amounts in the range 0.1 to 2% by weight.

The invention is illustrated by the Examples given below in which percentages are by weight. The deodorancy test referred to in the Examples was carried out as described below over five consecutive days on a panel of about 24 or more subjects.

DEODORANCY TEST

Day 1

After washing and drying his axillae an operator applies a placebo aerosol product to each axilla (a 2 seconds spray from about 15 cms). The panellist is then

| Placebo Product | |
|---|---|
| | % |
| Isopropyl myristate | 1.0 |
| Perfume | 0.44 |
| Propellant[1] to | 100.0 |

[1]as in Example 1

Day 2

With the panellist's shirt or blouse removed and his arms raised above his head each assessor (of which there are at least three) sniffs both the panellist's axillae and decides which side has the stronger underarm odour and records the score to indicate whether the right or left axilla had the stronger odour or whether the odours were equally strong. The panellist then assesses his own axillae in the same way.

After these assessments the procedure for Day 1 is repeated.

Day 3

The odour assessments of Day 2 are repeated. The washing and spraying of Day 1 is again repeated except that instead of applying the placebo product, the test product and control product are applied. To one preselected random group of panellists the test and control products are applied to the left and right axillae, respectively, and to the remaining panellists (a group of substantially the same size as the first mentioned group) the test and control products are applied on the right and left sides, respectively. A panellist's side to which the test product is applied is referred to as the test side and the side to which the control product is applied is referred to as the control side. The test and control products are applied in identical manner and typical of normal consumer usage. In the case of aerosol products they were applied in the same way as the placebo product.

Day 4

The procedure of Day 3 is repeated.

Day 5

The assessments as conducted on Day 2 are repeated.

From the scores obtained in the above test a Merit Score for the test product was calculated indicating the magnitude of the difference in the deodorancy effects between the test and control products.

Merit Score

The Merit Score associated with a test product is given by the expression $$\frac{100}{T}(A - B - C + D)$$

where
- A is the number of scores of the test side having the stronger odour when the placebo product is applied to both sides.
- B is the number of scores of the control side having the stronger odour when the placebo product is applied to both sides.
- C is the number of scores of the test side having the stronger odour when test and control products are applied.
- D is the number of scores of the control side having the stronger odour when test and control products are applied.
- T is the total number of assessments including those where the two sides are judged to be equal.

This Merit Score thus takes into account the decrease in the percentage of observations of the test side having the stronger odour $$\left(\frac{100}{T}(A-C)\right)$$

and the increase in the percentage of observations of the control side having the stronger odour $$\left(\frac{100}{T}(D-B)\right).$$

Thus the Merit Score indicates the difference in efficacy between test and control products.

Significance Testing

Provided the distribution of the placebo scores on Days 2 and 3 are not significantly different at the 5% level they are combined, and the same is done for the scores for Days 4 and 5, the combined scores for Days 4 and 5 then being compared with the combined scores for Days 2 and 3. All significance testing is done by the Kolmogorov-Smirnov analysis (see "Nonparametric Statistics for the Behavioral Sciences", International Student Edition, by S. Siegel, pages 127–136, published by McGraw-Hill and Kogakusha). All Merit Scores of 20 or more quoted hereinafter were statistically significant at the 5% level.

EXAMPLE 1

An aerosol deodorant spray was made having the following composition

|  | % |
| --- | --- |
| Magnesium oxide (heavy) | 4.5 |
| Isopropyl myristate | 6.0 |
| Pyrogenic silica (Aerosil 200) | 0.45 |
| Propellant to | 100.00 |

The magnesium oxide had an average particle size of about 40 microns and consisted of particles essentially in the range of 10 to 70 microns. Its surface area was about 25 m$^2$/g. The same magnesium oxide was employed in the subsequent examples.

The propellant consisted of a mixture of equal parts by weight of Propellant 11 (trichlorofluoromethane) and Propellant 12 (dichlorodifluoromethane).

The composition was prepared by first making a suspension concentrate by blending and homogenising all the ingredients except the propellant. The concentrate was placed in a container which was then sealed with a suitable aerosol valve and pressurized with the propellant.

The above product was tested for deodorancy by the deodorising test described above using as control product Control Product A having the following composition.

| Control Product A | |
| --- | --- |
|  | % |
| Industrial methylated spirit | 15.0 |
| Isopropyl myristate | 0.6 |
| Propellant[1] to | 100.0 |

[1]as in Example 1

The product of Example 1 had a Merit Score of 45.

In a second deodorancy test conducted as above save that the placebo product was used as the control, the Example 1 product had a Merit Score of 56.

EXAMPLE 2

An aerosol deodorant spray was made as in Example 1 except that the magnesium oxide was replaced by the same weight of basic magnesium carbonate.

In the deodorancy test using the placebo product as the control product, the product of this Example had a Merit Score of 31.

EXAMPLE 3

An aerosol deodorant spray was made having the following composition.

|  | % |
| --- | --- |
| Magnesium oxide | 1.5 |
| Industrial methylated spirit | 3.0 |
| Hydrophobic clay (Bentone 38) | 0.3 |
| Cetyl alcohol | 0.5 |
| Dipropylene glycol | 0.3 |
| Aqueous ethyl alcohol (92% alcohol) | 0.15 |
| Water-absorbent polymer | 1.0 |
| Isopropyl myristate | 2.0 |
| Propellant[1] to | 100.0 |

[1]as in Example 1

The water-absorbent polymer was that available commercially under the trade name "Permasorb 30 Cosmetic Grade" from the National Starch and Chemical Corporation. It is a potassium salt of a polyacrylic acid cross-linked by aluminium ions and is generally described in U.S. Pat. No. 4,090,013.

The composition was prepared by first blending the isopropyl myristate, dipropylene glycol, cetyl alcohol and Bentone 38 in a high shear mixer to form a gel. While continuing to shear the mixture the aqueous ethanol was added to stiffen the gel. The water-absorbent polymer was blended into the gel until a smooth cream was formed and similarly for the magnesium oxide. The final mixture together with the industrial methylated spirit were added to an aerosol container which was sealed with an aerosol valve and pressurized with the propellant.

The product was tested in the deodorancy test using as control the Control Product A. The product of the invention had a Merit Score of 29.

The product of this example was also compared in the deodorancy test with a conventional antiperspirant-/deodorant aerosol powder spray based on aluminium chlorhydrate. This product, referred to herein as Control Product B, had the following composition.

| Control Product B | |
| --- | --- |
|  | % |
| Aluminium chlorhydrate | 3.75 |
| Isopropyl myristate | 4.92 |
| Pyrogenic silica (Aerosil 200) | 0.31 |
| Propellant[1] to | 100.00 |

[1]as in Example 1

The product of the invention had a Merit Score of 1 and there was no significant difference in deodorancy between the two products.

The product of this example modified by the inclusion of 0.44% perfume was compared with Control Product B, similarly modified by inclusion of the same amount of the same perfume, in a consumer test employing a panel of 700 subjects over a period of 6 weeks. No statistically significant difference between the deodorant properties of the two products was found.

It may be mentioned that in the consumer test referred to a further test product employed was one essentially the same as the modified Example 3 product but employing zinc ricinoleate (as commercially available under the trade name "Grillocin HY65") in place of the magnesium oxide. This product was found to be significantly deficient in deodorant properties compared to the control product.

Examples of other suitable water-absorbent polymers that may be used in place of the above polymer are cross-linked carboxymethyl starch as described in German patent application No. 2 702 781, the cross-linked saponified copolymer of acrylic acid and a vinyl ester available commercially under the trade name Hydrogel S-50 from the Sumitomo Chemical Company, and the cross-linked acrylic polymer available commercially as Polymer XD-857.01 from the Dow Chemical Corporation.

EXAMPLE 4

An aerosol deodorant spray was made having the following composition

|  | % |
| --- | --- |
| Magnesium oxide | 2.0 |
| Isopropyl myristate | 3.0 |
| Cetyl alcohol | 0.5 |
| Aqueous ethanol (92% ethanol) | 0.3 |
| Hydrophobic clay (Bentone 38) | 0.6 |
| Industrial methylated spirit | 25.0 |
| Propellant[1] to | 100.0 |

[1]as in Example 1

This product was made by a method similar to that described above for the product of Example 3.

The product was tested for deodorancy using the above test method against Control Product A. The product of the invention had a Merit Score of 36.

EXAMPLE 5

An aerosol deodorant spray was made having the following composition

|  | % |
| --- | --- |
| Magnesium oxide | 2.0 |
| Isopropyl myristate | 2.0 |
| Pyrogenic silica (Aerosil 200) | 0.4 |
| Industrial methylated spirit | 19.0 |
| Water | 52.25 |
| Dimethyl ether to | 100.0 |

This product was made following the procedure described in Example 1, the final stage being the pressurising of the aerosol container with the dimethyl ether propellant.

The product was tested for deodorancy using the above test method against Control Product A. The product of the invention had a Merit Score of 25.

EXAMPLE 6

A deodorant roll-on product was made having the following composition

|  | % |
| --- | --- |
| Magnesium oxide | 20.0 |
| Isopropyl myristate | 20.0 |
| Hydrophobic clay (Bentone 38) | 2.0 |
| Cetyl alcohol | 2.0 |
| Aqueous ethanol (92% ethanol) | 1.0 |
| Industrial methylated spirit to | 100.0 |

The composition was prepared by first blending the isopropyl myristate, Bentone 38 and the cetyl alcohol in a high shear mixer to form a gel. While continuing to shear the mixture the aqueous ethanol was added to stiffen the gel. The magnesium oxide was then blended into the gel until a smooth cream was formed. This mixture and the industrial methylated spirit were then mixed and filled into roll-ball applicators.

The product was tested for deodorancy against roll-on Control Product C using the above test procedure. Control Product C had the following composition

| Control Product C |  |
| --- | --- |
|  | % |
| Isopropyl myristate | 25.0 |
| Hydrophobic clay (Bentone 38) | 2.5 |
| Cetyl alcohol | 2.5 |
| Aqueous ethanol (92% ethanol) | 1.3 |
| Industrial methylated spirit to | 100.0 |

In the deodorancy test the product of the invention had a Merit Score of 48.

EXAMPLE 7

The following is the composition of a roll-on deodorant product based on lanthanum oxide.

|  | % |
| --- | --- |
| Lanthanum oxide | 20.0 |
| Isopropyl myristate | 20.0 |
| Hydrophobic clay (Bentone 38) | 2.0 |
| Cetyl alcohol | 2.0 |
| Aqueous ethanol (92% ethanol) | 1.0 |
| Industrial methylated spirit to | 100.0 |

In the deodorancy test using as control roll-on Control Product C this product had a Merit Score of 38.

Similar products may be obtained by replacing the lanthanum oxide by lanthanum hyroxide or lanthanum carbonate.

EXAMPLE 8

The following is a deodorant roll-on formulation containing a water-absorbent resin.

|  | % |
| --- | --- |
| Lanthanum carbonate | 20.0 |
| Water absorbent resin[1] | 15.0 |
| Isopropyl myristate | 20.0 |
| Hydrophobic clay (Bentone 38) | 2.0 |
| Aqueous ethanol (92% ethanol) | 1.0 |
| Perfume | 1.0 |
| Industrial methylated spirit to | 100.0 |

[1]as in Example 3

The composition is prepared by first blending the isopropyl myristate and Bentone 38 in a high shear mixer to form a gel. While continuing to shear the mixture the aqueous ethanol is added to stiffen the gel. The water-absorbent polymer is blended into the gel until a smooth cream was formed and similarly for the lanthanum carbonate. The final mixture is then blended with the perfume and the industrial methylated spirit and poured into a roll-ball applicator.

EXAMPLE 9

This is an example of a deodorant product of the invention in the form of a stick.

|  | % |
| --- | --- |
| Magnesium oxide | 20.0 |
| Water-absorbent polymer[1] | 15.0 |
| Sodium stearate | 5.0 |
| Glycerine | 3.0 |
| Ethylene glycol monoethyl ether | 2.5 |
| Industrial methylated spirit to | 100.0 |

[1] as in Example 3

Various other comparative tests have been carried out.

Comparative Test I

A product the same as that of Example 1 save that it contained sodium bicarbonate in place of magnesium oxide was compared with Control Product A. The product containing sodium bicarbonate had a Merit Score of 23.

Comparative Test II

A body powder comprising 97% talc and 3% light magnesium oxide was compared with a control product based solely on talc. The magnesium oxide-containing powder had a Merit Score of minus 11 and was significantly worse than the control product.

Comparative Test III

In this test the control product was the placebo product described above and the test product had the following composition:

|  | % |
| --- | --- |
| Isopropyl myristate | 9.0 |
| Pyrogenic silica (Aerosil 200) | 1.5 |
| Propellant[1] to | 100.0 |

[1] as in Example 1

The test product had a Merit Score of minus 17 and was significantly worse than the control product.

Comparative Test IV

A product the same as that of Example 3 but modified by replacing the magnesium oxide by zinc ricinoleate (as available commercially under the trade name "Grillocin HY65") was compared with Control Product A in the deodorancy test. The test product containing zinc ricinoleate as the deodorant active had a Merit Score of minus 3 and there was no significant difference in deodorancy between the two products.

The compatability of a deodorant active material and a water-absorbent polymer may be determined by the following test.

Compatability Test

A slurry is prepared by adding 40 ml of a 0.1 molar sodium chloride solution to 1 g of absorbent polymer and 2 g of deodorant active material. The slurry so formed is left to equilibrate for 1 hour after which time a sample is transferred to a weighed sintered glass tube (weight $W_1$) which is then placed in a centrifuge tube and centrifuged at 3000 rpm for 1.25 hours in a MSE Super Minor branch standard swing arm centrifuge. The sintered tube is then reweighed (weight $W_2$) and placed in a vacuum oven at 60° C. until dried to constant weight (weight $W_3$). The retention capacity ($RC_1$) of the polymer in the presence of the deodorant active material is given by the expression $$\frac{W_2 - W_3}{W_3 - W_1}$$

The retention capacity ($RC_2$) of the polymer in the absence of the deodorant active material is determined in a similar manner. The effective absorbency (EA) of the polymer in the presence of the deodorant active material is given by $100 \times RC_1/RC_2$. Table 1 below gives the retention capacities of the polymers referred to in Example 3 in the presence of magnesium oxide as deodorant active material. The effective absorbency values are also given.

TABLE 1

|  | Absorbent Polymer | | | |
| --- | --- | --- | --- | --- |
|  | A | B | C | D |
| $RC_1$ value | 29.4 | 6.2 | 27.9 | 19.0 |
| $RC_2$ value | 31.5 | 8.7 | 20.8 | 21.7 |
| EA value | 93% | 71% | 134% | 88% |

Polymer A is the absorbent known as "Permasorb 30 Cosmetic Grade".

Polymer B is a cross-linked carboxymethyl starch as described in German patent application No. 2 702 781.

Polymer C is the absorbent known as "Hydrogel S-50

Polymer D is the absorbent known as "Polymer XD-857.01".

The retention capacities and effective absorbency values for polymers A and B in combination with various other deodorant active materials of this invention are given in Table II. This table includes data for the widely used deodorant active materials aluminium chlorhydrate and zinc phenolsulphonate.

TABLE II

|  | Absorbent Polymer | | | |
| --- | --- | --- | --- | --- |
|  | A | | B | |
| Deodorant Active Material | $RC_1$ value | EA value | $RC_1$ value | EA value |
| Magnesium carbonate (basic) | 13.2 | 42% | 17.1 | 197% |
| Magnesium hydroxide | 40.2 | 128% | 16.6 | 191% |
| Lanthanum carbonate | 12.0 | 38% | 6.0 | 69% |
| Lanthanum oxide | 14.4 | 46% | 5.8 | 67% |
| Aluminium chlorhydrate | 8.4 | 27% | 1.4 | 16% |
| Zinc phenolsulphonate | 0.4 | 1% | 3.3 | 38% |

The present invention thus allows the formulation of compositions containing a polymer for absorbing perspiration and a non-bactericidal deodorant active material to give a combination exhibiting both good deodorancy and relatively high absorbency.

What is claimed is:

1. A deodorant lotion, stick or aerosol composition for reducing axillary body odor comprising a suspension of an effective amount of a particulate deodorant active material in a physiologically acceptable carrier liquid or gel medium containing less than 80% water by weight of the carrier medium, wherein said deodorant active ingredient is selected from the group consisting of the oxides of magnesium and lanthanum and mixtures thereof, and wherein the deodorant composition does not suppress the secretion of perspiration.

2. A deodorant composition as claimed in claim 1 wherein the deodorant active powder is present in an amount of 0.5 to 30% by weight of the composition.

3. A deodorant composition as claimed in claim 1 wherein the deodorant active material is magnesium oxide.

4. A deodorant lotion, stick or aerosol composition for reducing axillary body odor comprising a suspension of an effective amount of a particulate deodorant active material in a physiologically acceptable carrier liquid or gel medium containing less than 80% water by weight of the carrier medium, wherein said deodorant active material is basic magnesium carbonate, and wherein the deodorant composition does not suppress the secretion of perspiration.

5. A deodorant composition as claimed in claim 1 wherein the carrier medium is substantially anhydrous and wherein the composition also contains an effective amount of a particulate prespiration-absorbing anionic polyelectrolyte.

6. A deodorant composition as claimed in claim 5 wherein the anionic polyelectrolyte amounts to 0.5 to 30% by weight of the composition.

7. A deodorant composition as claimed in claim 5 wherein the anionic polyelectrolyte is a salt of a polyacrylic acid cross-linked with aluminium ions.

8. A deodorant composition as claimed in claim 1 wherein the composition also comprises an effective amount of a normally gaseous propellant and is packaged in an aerosol container to form a deodorant spray product.

9. A deodorant composition as claimed in claim 1 wherein the carrier liquid is selected from $C_2$–$C_4$ aliphatic alcohols and mixtures thereof with water.

10. A deodorant composition as claimed in claim 9 wherein the composition also comprises a thickening agent and is packaged in a roll-on applicator.

11. A process for inhibiting axillary odour comprising applying to an axilla a deodorant composition as claimed in claim 1.

12. A deodorant lotion, stick or aerosol composition for reducing axially body odor comprising a suspension of an effective amount of a particulate deodorant active material in a physiologically acceptable carrier liquid or gel medium containing less than 80% water by weight of the carrier medium, wherein said deodorant active ingredient is selected from the group consisting of the oxides and carbonates of magnesium and lanthanum and mixtures thereof, the deodorant composition containing essentially no astringent aluminum salts with antiperspirant effect and wherein the deodorant composition does not suppress the secretion of perspiration.

13. A method for reducing axillary body odor comprising applying to the axillae a deodorant lotion, stick or aerosol composition comprising a suspension of an effective amount of a particulate deodorant active material in a physiologically acceptable carrier liquid or gel medium containing less than 80% water by weight of the carrier medium, wherein said deodorant active ingredient is selected from the group consisting of the oxides, hydroxides and carbonates of magnesium and lanthanum and mixtures thereof, and wherein the deodorant composition does not suppress the secretion of perspiration.

14. A method for reducing axillary body odor comprising applying to the axillae a deodorant lotion, stick or aerosol composition comprising a suspension of an effective amount of a particulate deodorant active material in a physiologically acceptable carrier liquid or gel medium containing less than 80% water by weight of the carrier medium, wherein said deodorant actove ingredient is magnesium carbonate, and wherein the deodorant composition does not suppress the secretion of perspiration.

* * * * *